(12) United States Patent
Vail et al.

(10) Patent No.: US 8,907,081 B2
(45) Date of Patent: Dec. 9, 2014

(54) LONG WAVELENGTH ABSORBING PORPHYRIN PHOTOSENSITIZERS FOR DYE-SENSITIZED SOLAR CELLS

(75) Inventors: Sean Andrew Vail, Vancouver, WA (US); David R. Evans, Beaverton, OR (US); Wei Pan, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 255 days.

(21) Appl. No.: 13/117,529

(22) Filed: May 27, 2011

(65) Prior Publication Data

US 2012/0302743 A1     Nov. 29, 2012

(51) Int. Cl.
    *C07D 487/22*      (2006.01)

(52) U.S. Cl.
    CPC .............. *C07D 487/22* (2013.01); *Y02E 10/542* (2013.01)
    USPC ......................................................... 540/145

(58) Field of Classification Search
    USPC ......................................................... 540/145
    See application file for complete search history.

(56) References Cited

U.S. PATENT DOCUMENTS

| 7,642,250 B2 | 1/2010 | Williams |
| 7,662,807 B2 | 2/2010 | Rimington et al. |
| 7,745,618 B2 | 6/2010 | Kiper et al. |
| 7,790,980 B2 | 9/2010 | Lee et al. |
| 7,799,910 B2 | 9/2010 | Lindsay et al. |

OTHER PUBLICATIONS

Hsieh et al. Synthesis and characterization of porphyrin sensitizers with various electron-donating substituents for highly efficient dye-sensitized solar cells. Journal of Materials Chemistry (2010), 20(6), 1127-1134.*

Hirao, T. , Sandwich dimer complexes of zinc porphyrins bearing three-dimensionally oriented redox-active n-conjugated pendant groups, Synlett, 2002, No. 3, p. 415-418.

D. L. Officer et al.. Coordination Chemistry Reviews 2004, 248, 1363.

* cited by examiner

*Primary Examiner* — Brian McDowell
(74) *Attorney, Agent, or Firm* — Law Office of Gerald Maliszewski; Gerald Maliszewski

(57) ABSTRACT

A long wavelength absorbing porphyrin/metalloporphyrin molecule is provided, made up of a porphyrin macrocycle and an anchor group for attachment to a substrate. A molecular linking element is interposed between the porphyrin macrocycle and the anchor group. The porphyrin/metalloporphyrin molecule also includes an (aminophenyl)amine group, either N,N-(4-aminophenyl)amine or N-phenyl-N-(4-aminophenyl)amine, where an amino moiety of the 4-aminophenyl group is derivatized by an element such as hydrogen, haloalkanes, aromatic hydrocarbons, halogenated aromatic hydrocarbons, heteroarenes, halogenated heteroarenes, or combinations of the above-mentioned elements.

8 Claims, 8 Drawing Sheets

YD11

YD12

YD13

2TPA

TPA-R

2TPA-R

Fig. 6B *(PRIOR ART)*
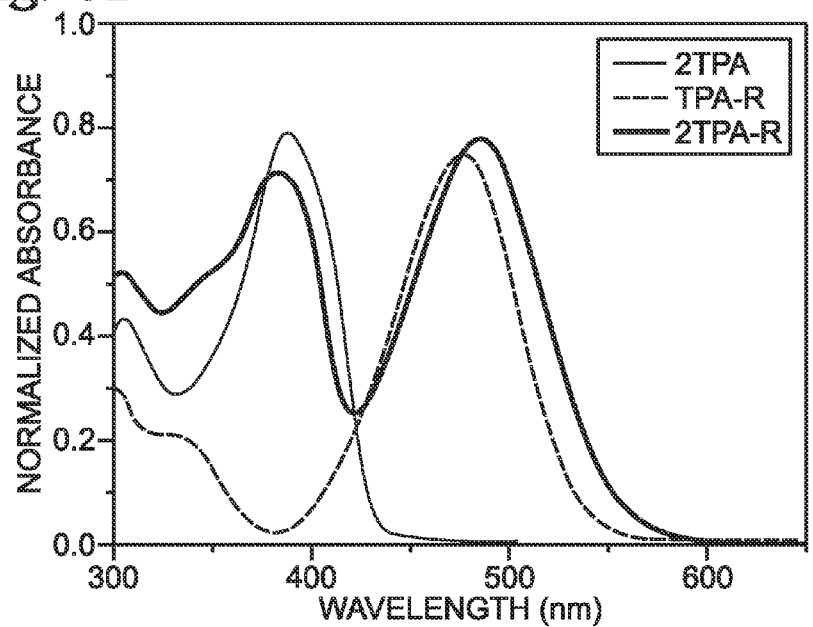
Fig. 8
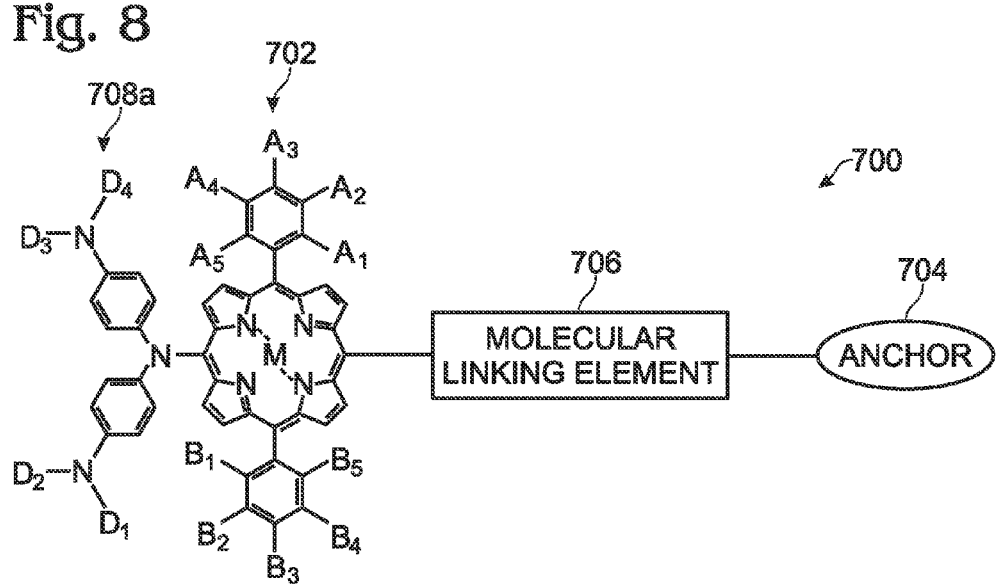

— OSCILLATOR STRENGTH vs. WAVELENGTH
--- BLACKBODY SPECTRUM (5250k)
— THEORETICAL ABSORPTION SPECTRUM
(OSCILLATOR STRENGTH X BLACKBODY SPECTRUM vs. WAVELENGTH)

— OSCILLATOR STRENGTH vs. WAVELENGTH
----- BLACKBODY SPECTRUM (5250k)
— THEORETICAL ABSORPTION SPECTRUM
(OSCILLATOR STRENGTH X BLACKBODY SPECTRUM vs. WAVELENGTH)

— OSCILLATOR STRENGTH vs. WAVELENGTH
----- BLACKBODY SPECTRUM (5250k)
— THEORETICAL ABSORPTION SPECTRUM
(OSCILLATOR STRENGTH X BLACKBODY SPECTRUM vs. WAVELENGTH)

LONG WAVELENGTH ABSORBING PORPHYRIN PHOTOSENSITIZERS FOR DYE-SENSITIZED SOLAR CELLS

BACKGROUND OF THE INVENTION

1. Field of the Invention

This invention generally relates to dye-sensitive light absorbing chemistry and, more particularly, to a porphyrin molecule useful in dye-sensitive light absorbing applications.

2. Description of the Related Art

Although chlorophyll, chlorophyll derivatives, and synthetic porphyrins have diverse chemical structures, they exhibit similar absorption characteristics over comparable wavelength ranges (typically $\lambda=350\text{-}700$ nm). Synthetic porphyrins (and their corresponding metalloporphyrins) consist of a conjugated $22\pi$ electron system, 18 of which are effectively delocalized to fit the Hückel requirement for aromaticity. In addition to their structural resemblance to natural chromophores such as chlorophyll, synthetic porphyrins are attractive candidates as light-harvesting materials due to their high structural stability, light absorption capabilities in the visible region, redox properties, and synthetic accessibility as compared to naturally occurring chromophores. Photoexcited processes involving porphyrins are facilitated by the highly delocalized $\pi$-system, which is capable of resisting major structural changes upon oxidation. Most importantly, the redox properties of porphyrins and metalloporphyrins are dramatically altered upon photoexcitation, which leads to the generation of porphyrin excited states that can be advantageous in photovoltaic (PV) cell applications.

The ability of porphyrins to efficiently harvest light over broad wavelength ranges has generated significant interest in their potential for solar applications over the last few decades. As a result, synthetic protocols towards the fabrication of "customized" porphyrin architectures have become well-established and have been widely adopted as conventional methods. In general, the electronic properties of porphyrins can be readily altered using a number of strategies including the following: functionalization and/or modification along the porphyrin periphery, insertion of transition metals into the macrocyclic core, complexation of metalloporphyrins with various ligands, etc. The strategic manipulation of porphyrin properties (optical absorption characteristics, photoexcited behaviors, etc.) through rational synthetic design has resulted in numerous publications, an overwhelming majority of which are academic in nature.

Most often, the desired enhancements accessible through chemical modification of porphyrins involve manipulation of light-harvesting (absorption) capabilities and/or excited-state behaviors (electron transfer, for example). For example, it is well-known that increasing the pi-conjugation extending from the porphyrin core can lead to enhanced absorption properties which may include (1) increased absorption over a particular wavelength range, (2) a broadening of optical absorption over wider wavelength ranges and/or (3) (bathochromic) shifting of absorption towards longer wavelengths. Furthermore, forward electron transfer processes from photoexcited porphyrin (donor) to acceptor moieties (metal oxides, fullerenes, carbon nanotubes, etc.) can be dramatically enhanced through the strategic introduction of electron transfer facilitating groups into the appropriate locations along the porphyrin core structure. In addition to exerting a favorable influence on electron transfer kinetics, some classes of functional groups can also dramatically improve the overall light harvesting capabilities of the porphyrin, whether it is in terms of increased absorption intensity over particular wavelengths, bathochromic shifting of absorption to longer wavelengths, or both.

At the present, ruthenium(II) bi- and polypyridyl complexes have proven to be the most efficient $TiO_2$ sensitizers in dye-sensitized solar cells (DSSC). However, only incremental improvements in the highest power efficiencies have been achieved within the past decade. Considering the facts that ruthenium(II) pyridyl dyes are expensive and ruthenium itself is a rare metal, there exists significant motivation to develop novel photosensitizers that either contain abundant, inexpensive metals or no metals at all, in response to this, several different classes of photosensitizer molecules have led to appreciably high efficiencies in dye-sensitized solar cells (DSSCs) including indoline (9%), coumarin (5.2%), hemicyanine (5.2%), squaraine (4.5%), phthalocyanine (3.5%) and porphyrins (from <1% to as high as 11%). See, respectively, D. L. Officer et al., *Coordination Chemistry Reviews* 2004, 248, 1363, D. L. Officer et al., *J. Phys. Chem., C* 2007, 111, 11760, E. W-G. Luau and CA. Yeh et al., *Chem. Eur. J.* 2009, 15, 1403, C-Y. Yeh and E. W-G. Luau et al., *Phys. Chem. Chem., Phys.* 2009, 11, 10270, and M. Grätzel et al., *Angew. Chem., Int. Ed.* 2010, 49, 6646.

FIGS. 1A and 1B are graphs depicting, respectively, the optical absorption spectrum for zinc tetraphenylporphyrin, and quantum efficiency (IPCE) values (%) for zinc tetraphenylporphyrin-$TiO_2$ as a function of optical absorption (prior art). As illustrated, extended $\pi$-conjugation in a zinc tetraphenylporphyrin-$TiO_2$ DSSC has previously shown to give rise to high internal photon to current efficiencies (IPCEs) at wavelengths in the 400-700 nm range, see D. L. Officer et al., *J. Phys. Chem, C* 2007, 111, 11760. Although chlorophyll and its derivatives have lower absorption at $\lambda=500\text{-}600$ nm (FIG. 1A) relative to $\lambda=450$ nm, DSSCs made with zinc tetraphenylporphyrin derivatives still exhibit high IPCE values at $\lambda=500\text{-}600$ nm (FIG. 1B). In this case, the appreciably high % IPCE between $\lambda=400\text{-}700$ nm can be attributed to broadened absorption for the zinc porphyrin and a favorable electronic communication between the zinc tetraphenylporphyrin and $TiO_2$ both of which benefit from extended conjugation between the donor and acceptor moieties. Based upon this, it is reasonable to assert the fact that the peak width and absorption edge(s) are the critical parameters when considering the optical absorption spectrum of a potential photosensitizer for DSSC applications. Under standard global AM 1.5 solar conditions, a short circuit photocurrent density (Jsc) of 14.0±0.20 mA/cm$^2$, an open circuit voltage (Voc) of 680±0.30 mV, and a fill factor (FF) of 0.74, corresponding to an overall conversion efficiency of 7.1%, was achieved using this porphyrin photosensitizer. In spite of this, the IPCE values for zinc tetraphenylporphyrin ($\approx 70\%$ at $\lambda=480$ and 580-640 nm, respectively) are still lower than that of ruthenium(II) pyridyl complexes. In addition, there is a decrease in IPCE values ($\approx 55\%$) at $\lambda\approx 480$ nm. Clearly, there exists the potential to improve IPCE values (possibly to ~80% or beyond).

FIG. 2 is a drawing depicting the molecular structure of a zinc porphyrin photosensitizer (YD1) that exhibits high efficiency (6%) in DSSC when co-adsorbed with chenodeoxycholic acid (CDCA) at ratios of 1:1 and 1:2 (ZnP:CDCA) (prior art). As reported by E. W-G. Diau and C-Y. Yeh et al., *Chem. Eur. J.* 2009, 15, 1403, this strategy takes advantage of (1) increased conjugation to both broaden and red-shift the absorption characteristics of the photosensitizer and (2) incorporation of a secondary electron transfer "facilitating" group (electron donor) to enhance the electron injection kinetics.

The photosensitizer design (D-P-B-A) takes advantage of a strongly absorbing porphyrin core (P), a conjugated bridge that broadens (red-shifts) the absorption capabilities of the photosensitizer while providing strong electronic coupling (B), a secondary electron transfer "facilitating," group (electron donor) to enhance the electron injection kinetics from the photoexcited porphyrin (D) and an anchoring group for strong attachment to $TiO_2$ (A).

FIGS. 3A, 3B, and 3C are three analogous porphyrin photosensitizer designs, respectively YD11, YD12, and YD13, based upon the architecture of FIG. 2 (prior art). As reported in the literature by C-Y. Yeh and E. W-G. Diau et al., *Phys. Chem. Chem. Phys.* 2009, 11, 10270, efficiencies between 6 to <7% were achieved in DSSCs using liquid electrolyte ($I^-/I_3^-$). Noteworthy is the fact that a DSSC utilizing YD12 as photosensitizer afforded an impressive efficiency of 6.91% versus 7.27% for ruthenium 719 dye (with added scattering layer) within the same cell configuration. The poor performance of YD13 can be reasonably attributed to rapid aggregate-induced energy transfer phenomena due to the presence of the anthracene group in the bridge.

FIG. 4 is a graph depicting the optical absorption spectra for YD11, YD12 and YD13 in ethanol (prior art). Zinc porphyrin photosensitizers YD11-YD13 exhibit the characteristic absorption features for both the Soret Band (400-520 nm) and the lower energy Q-Bands (580-700 nm) with significantly decreased absorption along the regions in between. The broadened and red-shifted absorption for YD11-YD13 is rationalized in terms of the structural design described above, which is a widely known strategy for enhancing absorption characteristics of porphyrins relative to "simple" porphyrins such as pristine zinc tetraphenylporphyrin.

FIG. 5 is the molecular structure of zinc porphyrin photosensitizer YD-2 (prior art). Most recently, M. Grätzel et al., *Angew. Chem., Int. Ed.* 2010, 49, 6646, have reported an exceptionally high efficiency of 11% for a member of the YD class (YD-2) in a double layer $TiO_2$ film, which is unprecedented for zinc porphyrin photosensitizers in DSSC. To increase the light-harvesting capacity of the devices, an 11 mm (transparent) $TiO_2$ film was coated with a 5 mm thin layer of 400 nm reflecting particles. The IPCE spectrum of the YD-2 device exhibits a broad absorption from 400 nm to 750 nm with an IPCE peak maximum greater than 90% at 675 nm. Jsc (18.6 mA/cm$^2$), Voc (0.77 V) and FF (0.764) were derived from the J-V curve, thus giving an overall power conversion efficiency of ~11% under illumination with standard AM 1.5 G simulated sunlight.

In light of the recent success using zinc porphyrin-based photosensitizers to achieve high efficiency, it is reasonable to assert that zinc porphyrins have the potential to rival the ruthenium-based dyes traditionally used in conventional DSSCs. In light of this, the rational design of novel porphyrin architectures for DSSC qualifies as an extremely valuable initiative.

Although the strategic introduction of strongly electron-donating di-aryl amine groups at the meso-position of a porphyrin is of interest, the application of aromatic amines to DSSC as co-sensitizers in general, as well the favorable photophysical behaviors obtained by incorporating aromatic amines into photosensitizer core structures, are well established.

Experimental results, reported by Guadiana et al., *J. Macromol. Sci, Part A Pure Appl. Chem,* 2003, A40, 1295, indicate that electron-donating (aromatic) amines that are anchored to the surface of $TiO_2$ as co-sensitizers effectively enhance the overall photovoltaic performances of DSSCs. Furthermore, they concluded that electron transfer from the amine to the photosensitizer dye is a key step in the photoexcited process.

FIGS. 6A and 6B are, respectively, the molecular structure and optical absorption spectra in dichloromethane of 2TPA, TPA-R and 2TPA-R (prior art). X. Yang, A. Hagfeidt and L. Sun et al., *Adv. Fund, Mater.* 2008, 18, 3461, report a dye (2TPA-R) containing two triphenylamine (TPA) units connected by a vinyl group and rhodanine-3-acetic acid as the electron acceptor. The experimental results suggest that intramolecular energy transfer processes contributed to the overall light-harvesting abilities of the donor-acceptor (D-A) dye in DSSC. Overall, 2TPA-R exhibited improved photovoltaic performance relative to TPA-R, which is indicative of the favorable enhancements accessible through the careful design of photosensitizers appended with an appropriate aromatic amine containing moiety. In this case, the enhanced performance most likely arises from both a combination of increased optical absorption and enhanced intramolecular electronics.

Although aromatic amines are widely-known to enhance the absorption and/or photoexcited behaviors of photosensitizer dyes, this is by no means a universal generalization. In fact, some ruthenium-based dyes covalently modified with aromatic amines (both conjugatively and non-conjugatively) have failed to produce any real improvements in photovoltaic performance relative to the original dyes (without aromatic amine).

In spite of the strong and broadened absorption for the zinc porphyrin photosensitizers described above, there still exists an overall deficiency in the ability of porphyrins to effectively harvest broad regions of the solar spectrum, especially at wavelengths exceeding 700 nm. Nevertheless, the more recently established potential for porphyrin photosensitizers has positioned this class of materials as a legitimate rival to traditional ruthenium-based dyes for DSSC applications.

It would be advantageous if a porphyrin photosensitizer could be synthesized that performs efficiently in DSSC due to contributions from absorption at wavelengths of 700 um and beyond.

SUMMARY OF THE INVENTION

The rational design of photosensitizers that can effectively harvest long wavelengths of light is critical for achieving highly efficient DSSCs. Although there exist a number of strategies for increasing photosenstizer absorption and manipulating electron injection kinetics/pathways, there are often drawbacks that arise from structural implications. For example, the synthesis of large, highly-conjugated photosensitizers is synthetically challenging (sometimes impossible) and often affords materials that are, at least for the most part, intractable. In general, these materials are impractical since they lack sufficient solubility for application and ultimately decrease the number of molecular photosensitizer units that can be employed due to the finite amount of space available for binding along the metal oxide surface (DSSC). In the case of porphyrins and metalloporphyrins, the core structure dominates the absorption and photoexcited-state behaviors of its derivatives although the strategic (covalent) introduction of the appropriate groups can provide a favorable (additive) effect in terms of optical absorption, forward electron transfer kinetics, and/or suppression of charge recombination. Unfortunately, the incorporation of photoactive moieties often leads to additional (unpredictable) photoexcited deactivation pathways which can be detrimental to photosensitizer performance in DSSC. In light of this, a class of porphyrin-based photosensitizer architectures is presented for which molecular simulations have calculated optical absorption capabilities far greater than those reported for the YD class of materials discussed in the Background Section, above.

As previously mentioned, the concept of incorporating aromatic amines in photosensitizer core structures in order to enhance performance is widely known. In addition, the fact that the existence of a high degree of conjugation between the photosensitizer and metal oxide surface (DSSCs) is critical for providing effective communication through the bridging element is common knowledge in photosensitizer and DSSC development. However, a critical consideration towards the design of highly efficient photosensitizers for DSSC applications involves the concept of orbital partitioning, which is characterized by both high HOMO coefficients on the donor moiety and high LUMO coefficients on the acceptor group within the same molecule. In fact, the high efficiency for ruthenium-based photosensitizers in DSSC can reasonably be attributed to HOMO and LUMO localization on the thiocyanate ligands and pyridyl anchor groups, respectively. In general, high degrees of orbital partitioning can increase the driving force (rates) for electron injection to $TiO_2$ from the photoexcited dye (LUMO) and may lead to lower rates for charge recombination between photoexcited dye (cations) and electrons in $TiO_2$ following charge separation.

Accordingly, a long wavelength absorbing porphyrin/metalloporphyrin molecule is provided made up of a porphyrin macrocycle, and an anchor group for attachment to a substrate. A molecular linking element is interposed between the porphyrin macrocycle and the anchor group. The porphyrin/metalloporphyrin molecule also includes an (aminophenyl)amine group, either N,N-(4-aminophenyl)amine or N-phenyl-phenyl-N-(4-aminophenyl)amine, where an amino moiety of the 4-aminophenyl group is derivatized by an element such as hydrogen, alkanes, haloalkanes, aromatic hydrocarbons, halogenated aromatic hydrocarbons, heteroarenes, halogenated heteroarenes, or combinations of the above-mentioned elements.

Additional details of the above-described porphyrin/metalloporphyrin molecule are presented below.

BRIEF DESCRIPTION OF THE DRAWINGS

FIGS. 6A and 6B are, respectively, the molecular structure and optical absorption spectra in dichloromethane of 2TPA, TPA-R and 2TPA-R (prior art).

FIG. 8 is a schematic of a molecular structure of porphyrin-based photosensitizer using N,N-(4-aminophenyl)amine as the electron-donating group on the porphyrin meso position.

DETAILED DESCRIPTION

Figure 7:
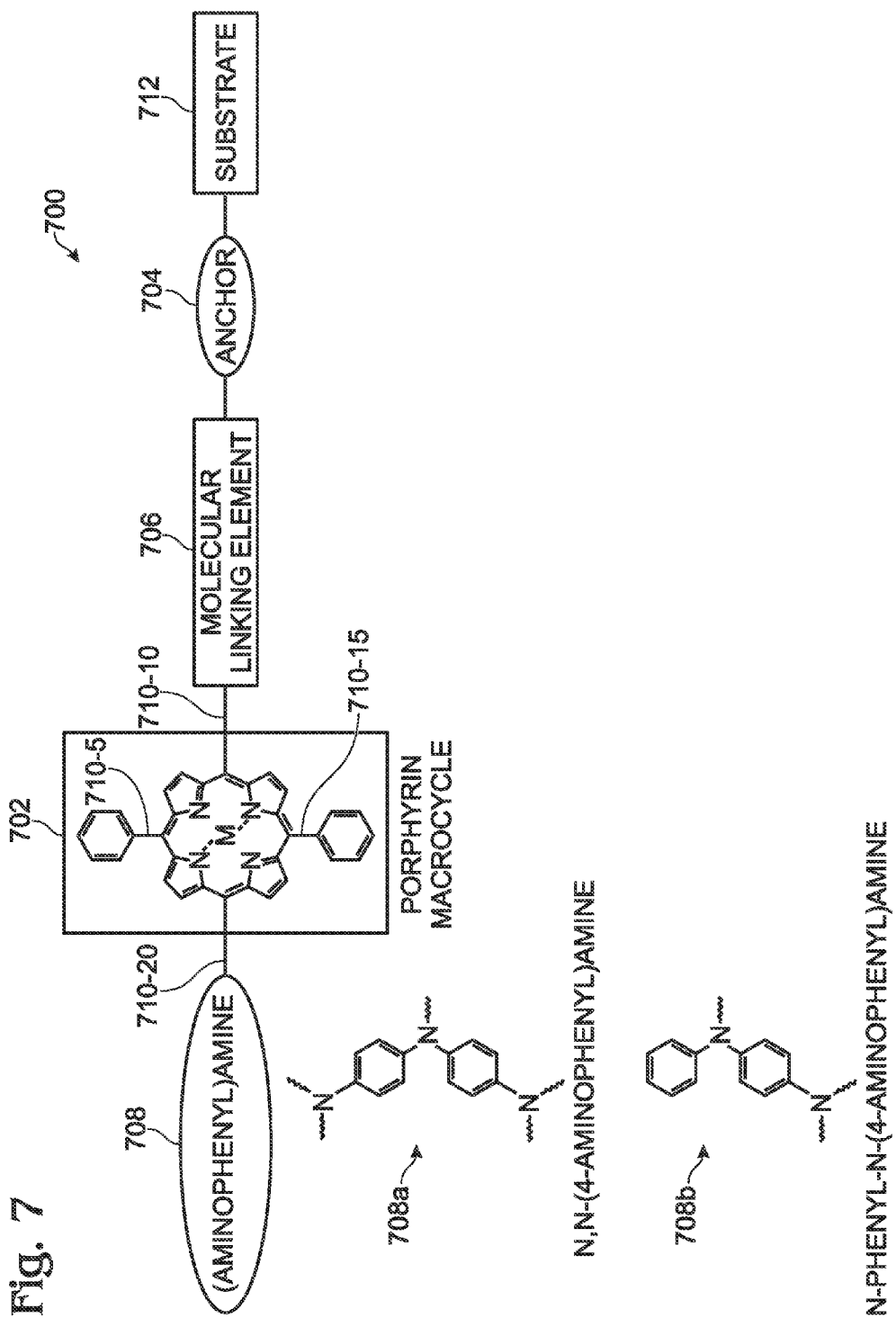
FIG. 7 is a diagram depicting a long wavelength absorbing porphyrin/metalloporphyrin molecule.

FIG. 7 is a diagram depicting a long wavelength absorbing porphyrin/metalloporphyrin molecule. The porphyrin/metalloporphyrin molecule 700 comprises a porphyrin macrocycle 702, and an anchor group 704 for attachment to a substrate. In one aspect, the porphyrin macrocycle 702 includes an "M" moiety such as $H_2$ or a metal. A molecular linking element 706 is interposed between the porphyrin macrocycle 702 and the anchor group 704. The porphyrin/metalloporphyrin molecule 700 also comprises an (aminophenyl)amine group 708 that may be either N,N-(4-aminophenyl)amine 708a or N-phenyl-N-(4-aminophenyl)amine 708b, where the amino moiety of the 4-aminophenyl group is derivatized by an element such as hydrogen, alkanes, haloalkanes, aromatic hydrocarbons, halogenated aromatic hydrocarbons, heteroarenes, halogenated heteroarenes, or combinations of the above-mentioned elements. As used herein, the term "element" is not defined as only an element of the periodic table, but may also refer to a molecule, combination of molecules, or combination of elements from the periodic table.

In one aspect, the molecular linking element 706 is a conjugated, nonconjugated, or combination of conjugated and nonconjugated classes of molecules. For example, the molecular linking element may be one of the following elements: linear alkanes, branched alkanes, cycloalkanes, (poly) cycloalkanes, cis- and trans-linear alkenes, cis- and trans-branched alkenes, linear alkynes, branched alkynes, (poly)alkynes, aromatic hydrocarbons, (poly)aromatic hydrocarbons, heteroarenes, (poly)heteroarenes, thiophenes, (poly)thiophenes, (poly)anilines, or combinations of the above-mentioned elements.

In another aspect, the porphyrin macrocycle 702 has four meso positions. With respect to nomenclature, these 4 meso positions are designated (or commonly referred to as) 5, 10, 15 and 20. Therefore, the four meso positions are labeled 710-5, 710-10, 710-15, and 710-20. The (aminophenyl)amine group 708 originates on one meso position of the porphyrin macrocycle (as shown, 710-20). The molecular linking element originates on a second meso position of the porphyrin macrocycle (as shown, 710-10). For example, the (aminophenyl)amine group 708 and molecular linking element 706 may originate on opposite meso positions of the porphyrin macrocycle 702, as shown.

In one aspect, the anchor group 704 is a chemical group capable of interacting with a substrate via chemical bonding, complexation, coordination, and any mode of interaction promoting communication between the porphyrin macrocycle 702 and a substrate, through the molecular linking element 706. For example, the anchor group 704 may be one of the following chemical groups: carboxylic acids, carboxylates, sulfonic acids, sulfonates, phosphonic acids, phosphonates, malonic acids, malonates, carboxylic acid anhydrides, lactones, cyanoacrylic acids, silanes, or combinations of the above-mentioned chemical groups.

In one aspect, the (aminophenyl)amine group 708 is N,N-(4-aminophenyl)amine 708a, with atoms $D_1$-$D_4$, where D is a chemical moiety such as hydrogen, alkanes, haloalkanes, aromatic hydrocarbons, halogenated aromatic hydrocarbons, heteroarenes, halogenated heteroarenes, or combinations of the above-mentioned chemical moieties.

Then, the porphyrin macrocycle 702 includes an "M" moiety such as $H_2$ or a metal, a first group $A_1$-$A_5$, and a second group $B_1$-$B_5$, where A and B are chemical moieties such as hydrogen, halogen, amino, alkyl, haloalkyl, alkoxy, haloalkoxy, aryl, haloaryl, aryloxy, haloaryloxy, heteroaryl, haloheteroaryl, heteroaryloxy, haloheteroaryloxy, or combinations of the above-mentioned chemical moieties.

In a different aspect, the (aminophenyl)amine 708 is N-phenyl-N-(4-aminophenyl)amine 708b, with $D_1$-$D_2$, where D is a chemical moiety such as hydrogen, alkanes, haloalkanes, aromatic hydrocarbons, halogenated aromatic hydrocarbons, heteroarenes, halogenated heteroarenes, combination of the above-mentioned chemical moieties. N-phenyl-N-(4-aminophenyl)amine 708b also includes $C_1$-$C_5$, where C is a chemical moiety such as hydrogen, halogen, amino, alkyl haloalkyl, alkoxy, haloalkoxy, aryl, haloaryl, aryloxy, haloaryloxy, heteroaryl, haloheteroaryl, heteroaryloxy, haloheteroarloxy, or combinations of the above-mentioned chemical moieties. Then, the porphyrin macrocycle 702 includes an "M" moiety such as $H_2$ or a metal, a first group $A_1$-$A_5$, and a second group $B_1$-$B_5$, where A and B are chemical moieties such as hydrogen, halogen, amino, alkyl, haloalkyl, alkoxy, haloalkoxy, aryl, haloaryl, aryloxy, haloaryloxy, heteroaryl, haloheteroaryl, heteroaryloxy, haloheteroaryloxy, and combinations of the above-mentioned chemical moieties.

In one aspect, the anchor group 704 interacts with a substrate 712 such as a metallic, organic, inorganic, organic-inorganic hybrid material, or combinations of the above-mentioned materials.

Functional Description

Molecular simulations have been used to calculate absorption/electronic properties for the above-described porphyrin architectures which exhibit unprecedented optical absorption characteristics (up to ~1150 nm).

FIG. 8 is a schematic of a molecular structure of porphyrin-based photosensitizer using N,N-(4-aminophenyl)amine 708a as the electron-donating group on the porphyrin meso position. In this aspect, $A_1$-$A_5$=hydrogen, halogen, amino, alkyl, haloalkyl, alkoxy, haloalkoxy, aryl, haloaryl, aryloxy, haloaryloxy, heteroaryl, haloheteroaryl, heteroaryloxy, haloheteroaryloxy, or combinations of the above-mentioned chemical moieties, $B_1$-$B_5$=hydrogen, halogen, amino, alkyl, haloalkyl, alkoxy, haloalkoxy, aryl, haloaryl, aryloxy, haloaryloxy, heteroaryl, haloheteroaryl, heteroaryloxy, haloheteroaryloxy, or combinations of the above-mentioned chemical moieties, $D_1$-$D_4$=hydrogen, alkanes, haloalkanes, aromatic hydrocarbons, halogenated aromatic hydrocarbons, heteroarenes, halogenated heteroarenes, or combinations of the above-mentioned chemical moieties, and M=$H_2$ or metal. The types of materials identified for the molecular linking element 706 and anchor 704 have been described above.

Figure 9:
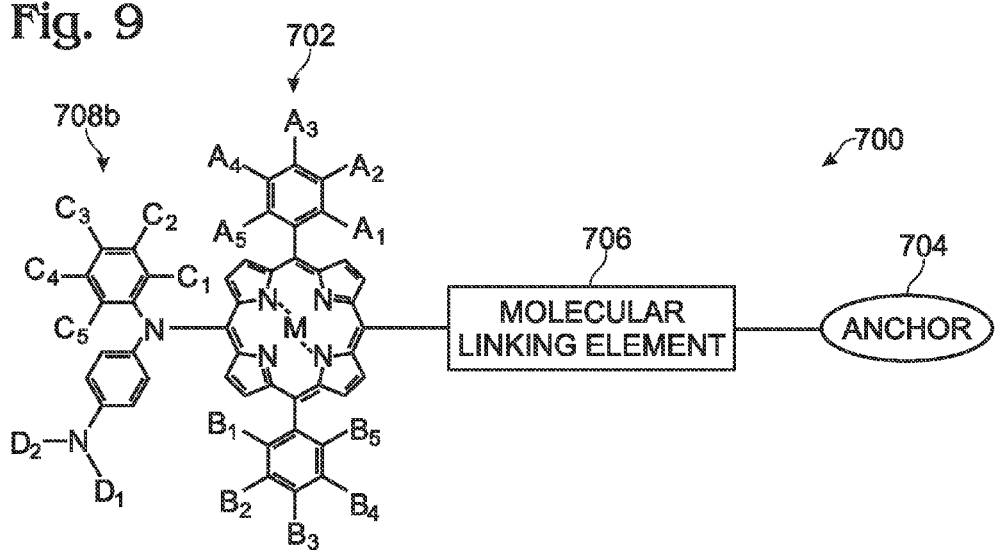
FIG. 9 is a schematic of a molecular structure of porphyrin-based photosensitizer using N-Phenyl-N-(4-aminophenyl)amine as the electron-donating group on the porphyrin meso position.

FIG. 9 is a schematic of a molecular structure of porphyrin-based photosensitizer using N-Phenyl-N-(4-aminophenyl)amine 708b as the electron-donating group on the porphyrin meso position. In this aspect, $A_1$-$A_5$=hydrogen, halogen, amino, alkyl, haloalkyl, alkoxy, haloalkoxy, aryl, haloaryl, aryloxy, haloaryloxy, heteroaryl, haloheteroaryl, heteroaryloxy, haloheteroaryloxy, or combinations of the above-mentioned chemical moieties, $B_1$-$B_5$=hydrogen, halogen, amino, alkyl, haloalkyl, alkoxy, haloalkoxy, aryl, haloaryl, aryloxy, haloaryloxy, heteroaryl, haloheteroaryl, heteroaryloxy, haloheteroaryloxy, or combinations of the above-mentioned chemical moieties, $C_1$-$C_5$=hydrogen, halogen, amino, alkyl, haloalkyl, alkoxy, haloalkoxy, aryl, haloaryl, aryloxy, haloaryloxy, heteroaryl, haloheteroaryl, heteroaryloxy, haloheteroaryloxy, or combinations of the above-mentioned chemical moieties, $D_1$-$D_2$=hydrogen, alkanes, haloalkanes, aromatic hydrocarbons, halogenated aromatic hydrocarbons, heteroarenes, halogenated heteroarenes, or combinations of the above-mentioned chemical moieties, and M=$H_2$ or metal. The types of materials identified for the molecular linking element 706 and anchor 704 have been described above.

Molecular simulations were carried out using a zinc diphenylporphyrin core with para-ethynylbenzoic acid as the molecular linking element and anchor group. Oscillator strengths were calculated with time dependent density functional theory (TDDFT) using a gradient corrected Becke-Lee-Yang-Parr (BLYP) functional. Calculated oscillator strengths were used to simulate absolute absorption (solid dark curve) and absorption spectra assuming a 5250K blackbody source (solid lighter curve), in all three cases, the blackbody source is represented by the dotted curve. Simulated spectra assuming a 50 nm Gaussian broadening for three different electron-donating groups are shown in FIGS. 10-12.

Figure 1A:
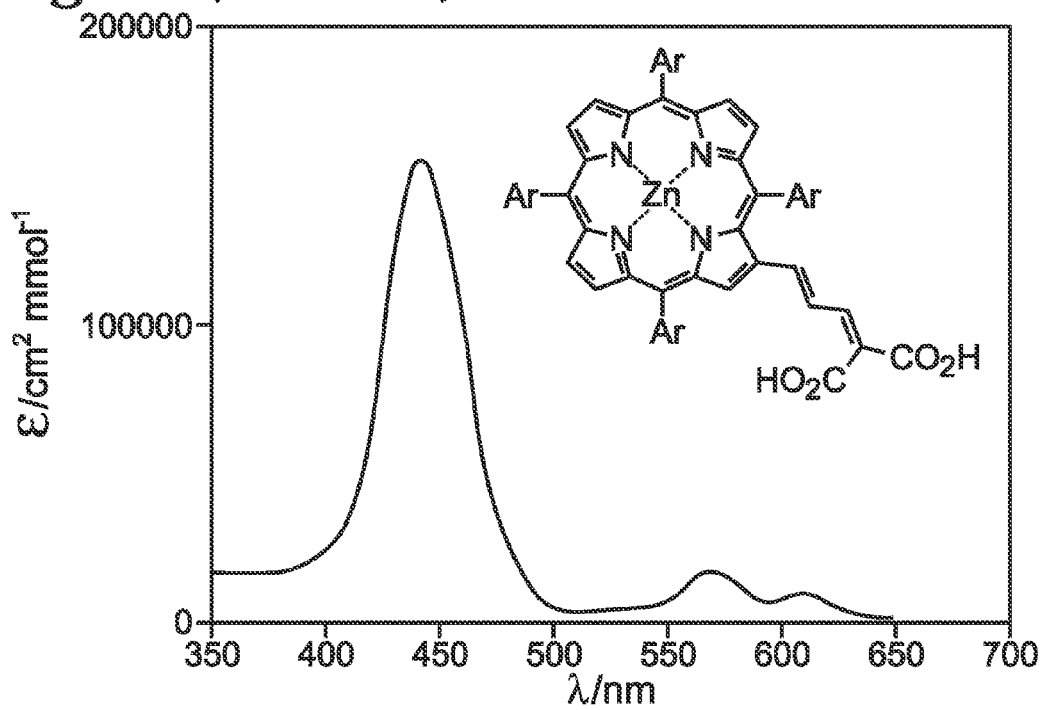
FIGS. 1A and 1B are graphs depicting, respectively, the optical absorption spectrum for zinc tetraphenylporphyrin, and quantum efficiency (IPCE) values (%) for zinc tetraphenylporphyrin-$TiO_2$ as a function of optical absorption (prior art).
Figure 1B:
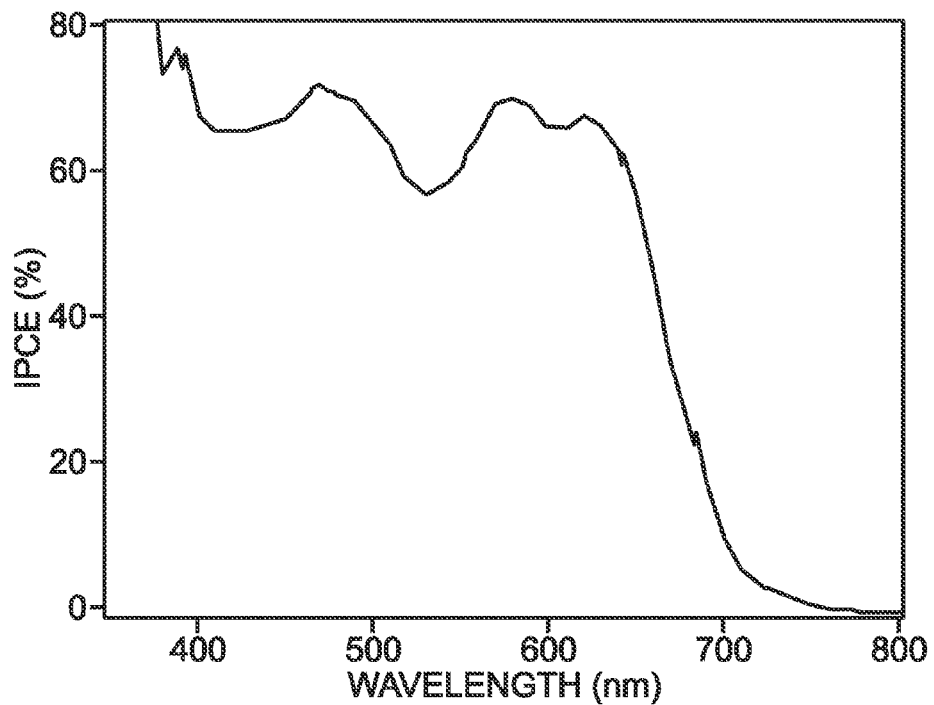
Figure 2:
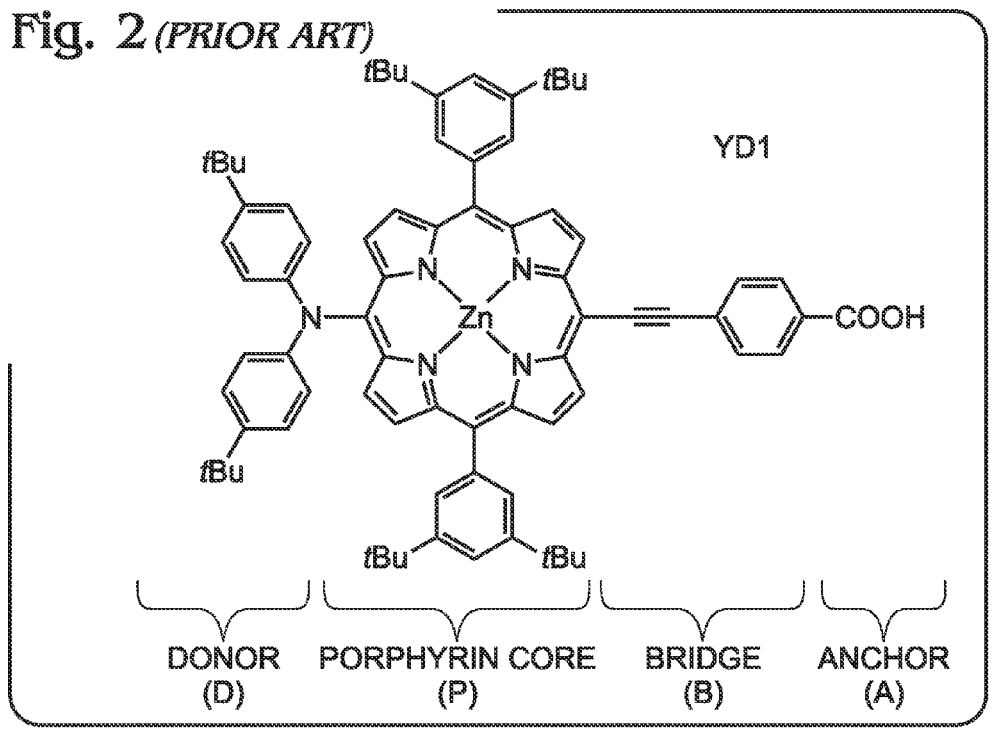
FIG. 2 is a drawing depicting the molecular structure of a zinc porphyrin photosensitizer (YD1) that exhibits high efficiency (6%) in DSSC when co-adsorbed with chenodeoxycholic acid (CDCA) at ratios of 1:1 and 1:2 (ZnP:CDCA) (prior art).
Figure 4:
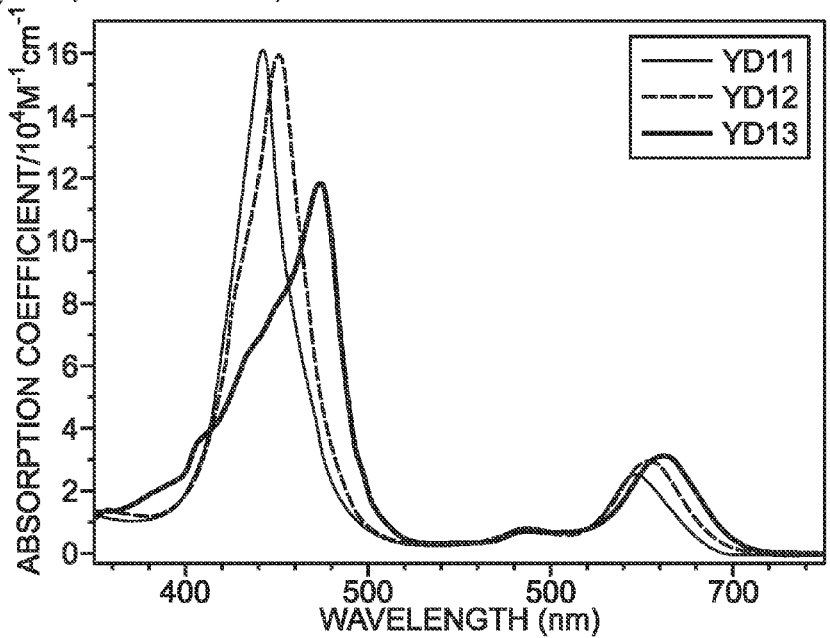
FIG. 4 is a graph depicting the optical absorption spectra for YD11, YD12 and YD13 in ethanol (prior art).
Figure 3A:
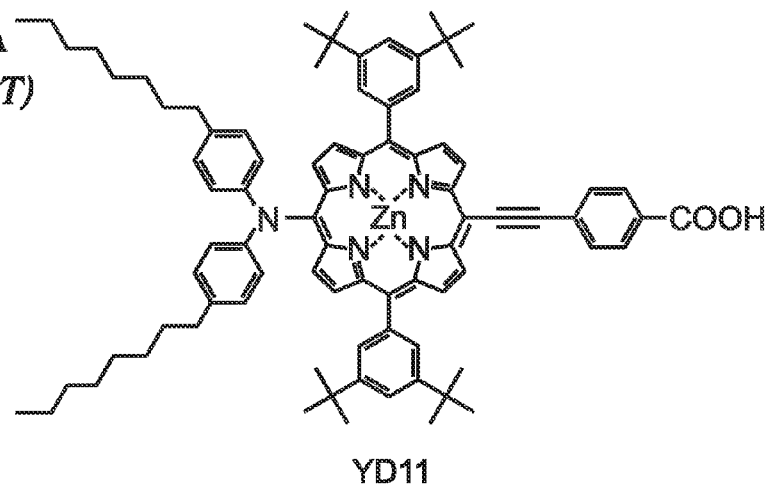
FIGS. 3A, 3B, and 3C are three analogous porphyrin photosensitizer designs, respectively YD11, YD12, and YD13, based upon the architecture of FIG. 2 (prior art).
Figure 3B:
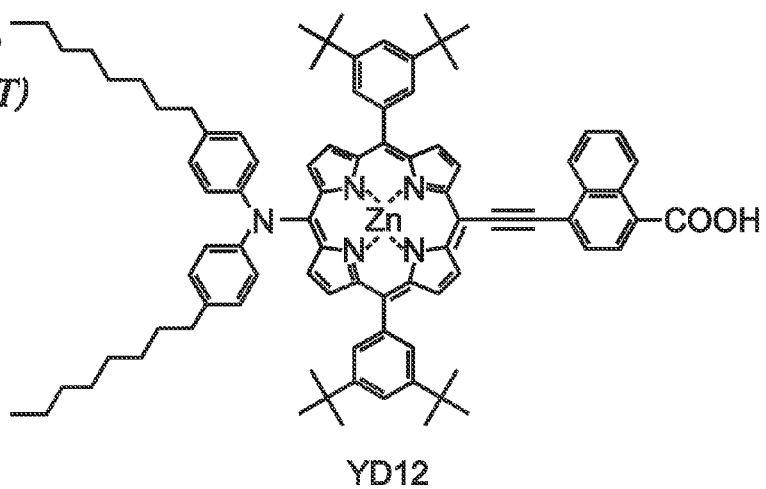
Figure 3C:
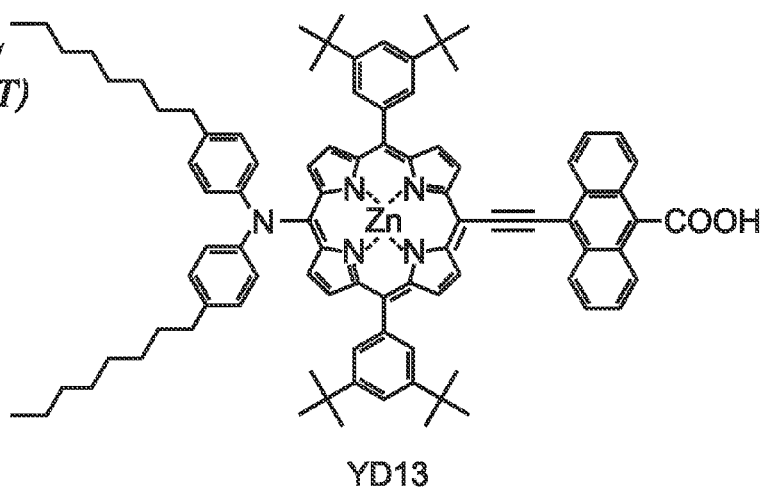
Figure 5:
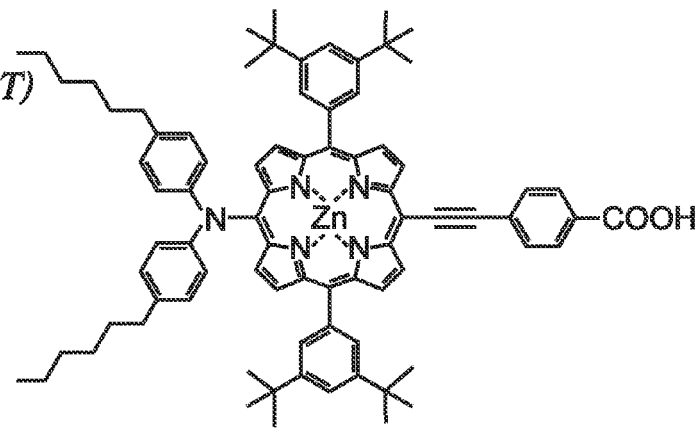
FIG. 5 is the molecular structure of zinc porphyrin photosensitizer YD-2 (prior art).
Figure 6A:
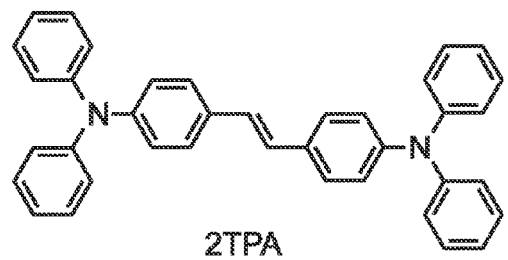
Figure 6A:
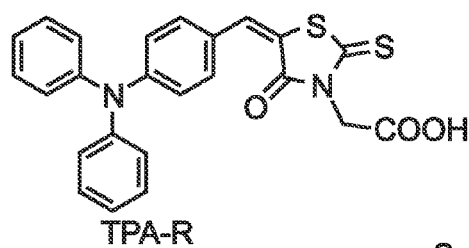
Figure 6A:
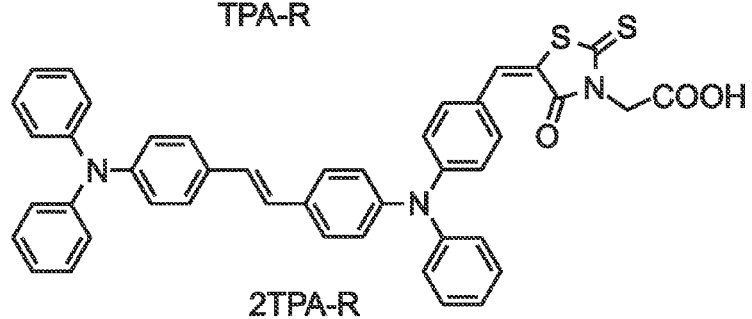
Figure 10:
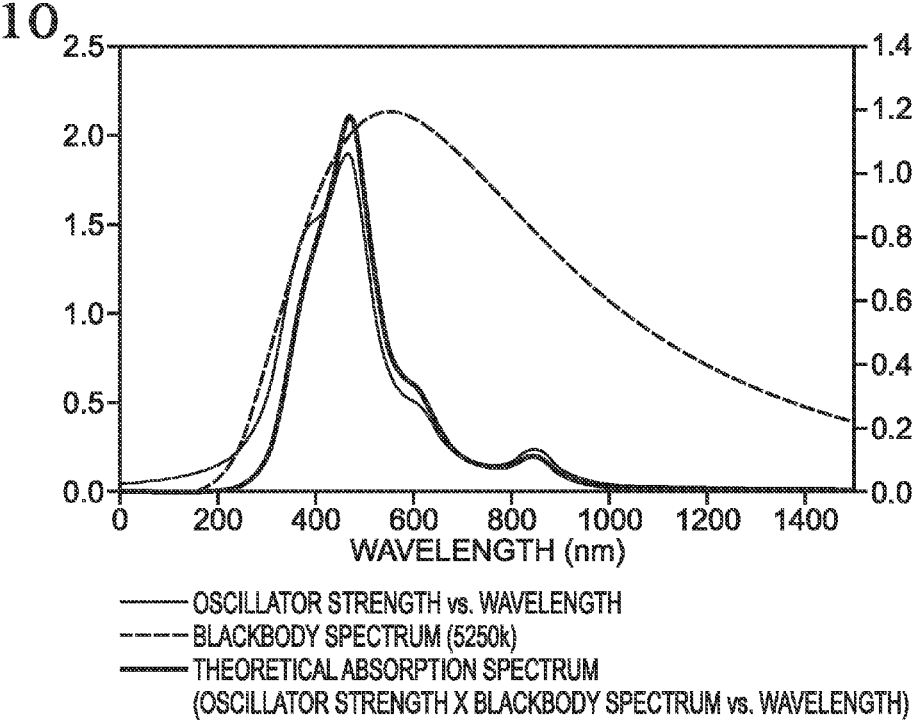
FIG. 10 is a simulated optical absorption spectrum for the YD class of porphyrin photosensitizers, which utilize meso-N,N-diphenylamine as the electron-donating group.

FIG. 10 is a simulated optical absorption spectrum for the YD class of porphyrin photosensitizers, which utilize meso-N,N-diphenylamine as the electron-donating group. In order to simplify the calculations, the tert-butyl groups and n-hexyl groups were omitted from the structure of YD-2 (see FIG. 5). Although the alkyl groups enhance the solubility of the porphyrin in organic solvents and may aid in the suppression of molecular aggregation, the overall contribution of these groups to the optical absorption properties of the porphyrin is negligible.

Figure 11:
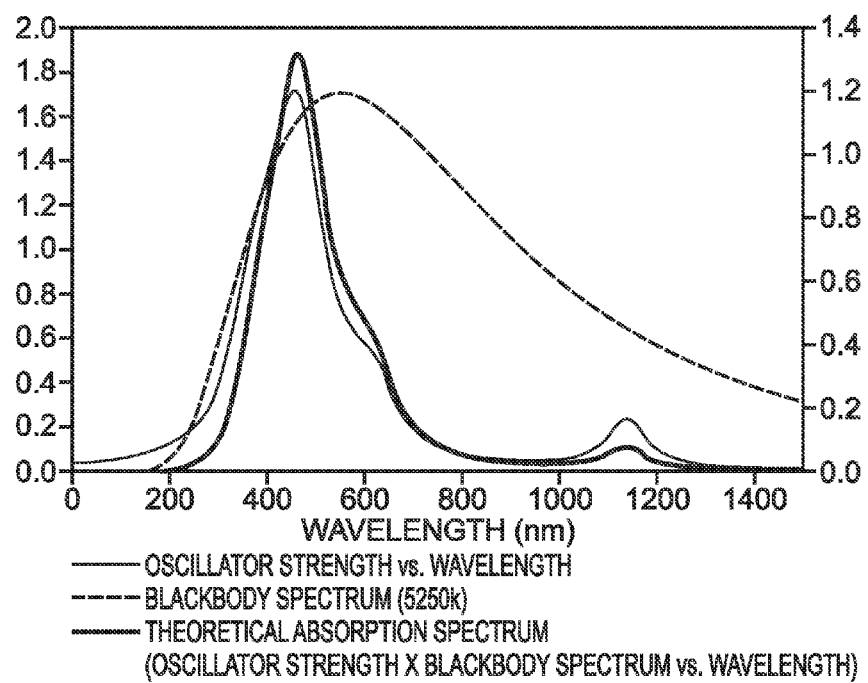
FIG. 11 is a simulated optical absorption spectrum for the class of porphyrin photosensitizers which utilizes meso-N,N-(4-nophenyl)amine as the electron-donating group.

FIG. 11 is a simulated optical absorption spectrum for the class of porphyrin photosensitizers which utilizes meso-N,N-(4-aminophenyl)amine as the electron-donating group. Using the molecular diagram in FIG. 8 as a guide, the structure is consistent with the following: $A_1$-$A_5$=H, $B_1$-$B_5$=H, $D_1$-$D_4$=H and M=zinc.

Figure 12:
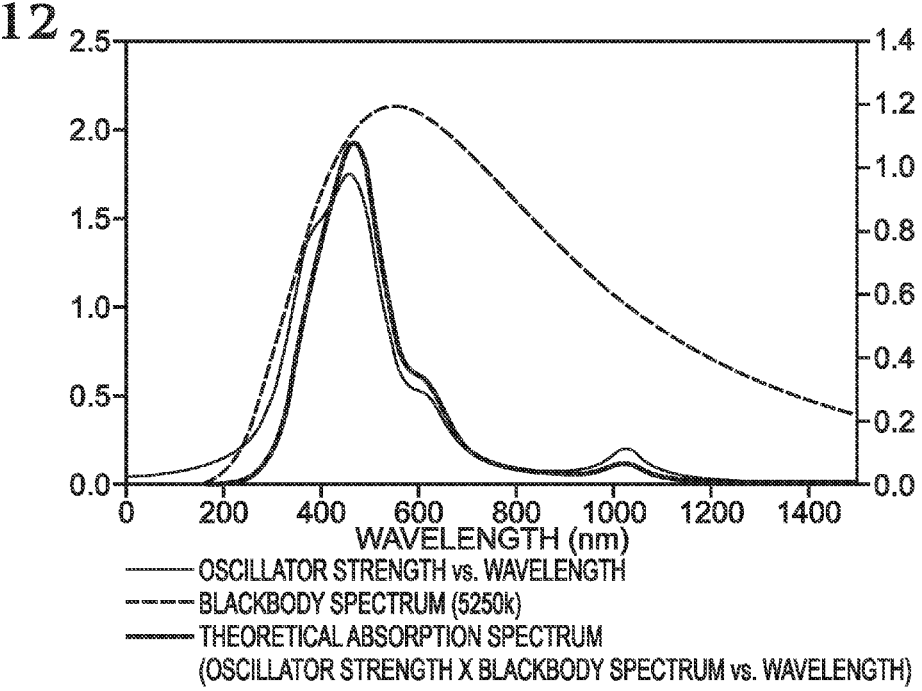
FIG. 12 is a simulated optical absorption spectrum for the class of porphyrin photosensitizers which utilizes meso-N-Phenyl-N-(4-aminophenyl)amine as the electro-donating group.

FIG. 12 is a simulated optical absorption spectrum for the class of porphyrin photosensitizers which utilizes meso-N-Phenyl-N-(4-aminophenyl)amine as the electron-donating group. Using the molecular diagram in FIG. 9 as a guide, the structure is consistent with the following: $A_1$-$A_5$=H, $B_1$-$B_5$=H, $C_1$-$C_5$=H, $D_1$-$D_2$=H and M=zinc.

Based upon the molecular simulations, it is evident that the porphyrin Soret Band (~450 nm) is essentially unaffected by changes in the nature of the electron-donating (meso-diphenylamine) group for the classes of YD, N,N-(4-aminophenyl)amine and N-phenyl-N-(4-aminophenyl)amine porphyrin photosensitizers respectively. In contrast, there is a dramatically red-shifted Q-band absorption along the series from the YD porphyrin (850 nm for meso-N,N-diphenylamine, FIG. 10) to N,N-(4-aminophenyl)amine (1150 nm for meso-N,N-(4-aminophenyl)amine, FIG. 11). N-phenyl-N-(4-aminophenyl)amine, which may be considered to be an "intermediate" between YD and N,N-(4-aminophenyl)amine, also shows significant red-shifted Q-band absorption (1050 nm for meso-N-Phenyl-N-(4-aminophenyl)amine, FIG. 12) relative to YD reference although to a lower extent than N,N-(4-aminophenyl)amine. Based upon the experimental optical absorption spectra for YD compounds reported in the literature, the simulation results may overestimate the bathochromic shift for the porphyrin Q-Band to some extent; however, the general trend indicated by meso-N,N-(4-aminophenyl)amine and meso-N-Phenyl-N-(4-aminophenyl)amine substitution is realistic. Therefore, the expected red-shifted absorption due to the meso-N,N-(4-aminophenyl)amine electron-donating group in N,N-(4-aminophenyl)amine can be conservatively estimated to be greater than 800 nm, thus, rendering this class of compounds appropriate as long wavelength absorber materials (400 to >800 nm) for DSSCs. In addition, similar calculations were made using a zinc metallated phthalocyanine core rather than diphenylporphyrin and a similar bathochromic shift was indicated. Therefore it is likely that such bathochromic shifts are characteristic of these electron-donating groups when suitably attached to a highly delocalized $\pi$-system core.

In one aspect, the porphyrin photosensitizer architectures exhibit 2 major characteristics. First, the design imparts a high degree of orbital partitioning (HOMO-LUMO energy distribution). Second, the absorption of a porphyrin material has been pushed towards longer wavelengths in order to more efficiently harvest broader and longer wavelength regions of the spectrum. To some extent, this is facilitated by the orbital partitioning described above, although there are some additional contributing factors which are linked in many ways to the structures. In general, porphyrins exhibit absorption in 2 discrete wavelength regions: strong absorption ~400-450 nm (Soret Band) and considerably weaker absorption at longer wavelengths (550-700 nm or Q-Band region). In almost all cases, the absorption in the 450-550 nm region (or along an even broader range of this intermittent region) approaches zero. In general, it is quite rare to find a porphyrin material that absorbs light to any significant extent beyond 700 nm and which, at the same time, meets the structural requirements to be promising as an efficient photosensitizer in DSSC, in fact, the "best" performing porphyrin-based photosensitizer in DSSC to date (~11% efficiency, 2010) demonstrates negligible absorption beyond 700 nm, although some residual absorption remains up to ~725 nm or perhaps slightly beyond.

A long wavelength absorbing porphyrin/metalloporphyrin molecule has been provided. Examples of particular derivatives have been presented to illustrate the invention. However, the invention is not united to merely these examples. Other variations and embodiments of the invention will occur to those skilled in the art.

We claim:

1. A zinc porphyrin molecule comprising:
   a zinc porphyrin with four meso positions defined as 5, 10, 15, and 20 meso positions; and,
   a bis(4-dimethylaminophenyl)amino group connected to a first meso position from the four zinc porphyrin meso positions.

2. The zinc porphyrin molecule of claim 1 further comprising:
   a molecular linking element connected to a second mesa position from the four zinc porphyrin mesa positions, the molecular linking element selected from a group consisting of alkenyl, alkynyl, aryl, heteroaryl, and combinations of the above-mentioned elements.

3. The zinc porphyrin molecule of claim 2 wherein the zinc porphyrin first meso position and second meso position are opposite meso positions, where the 5 meso position is defined as opposite the 15 meso position and the 10 meso position is defined as opposite the 20 meso position.

4. The zinc porphyrin molecule of claim 1 further comprising:
   a molecular linking element connected to a second meso position from the four zinc porphyrin meso positions, the molecular linking element selecting from a group consisting of alkenyl, alkynyl, aryl, heteroaryl, and combinations of the above-mentioned elements; and,
   an anchor group attached to the molecular linking element, the anchor group selected from a set consisting of carboxyl, sulfonyl, phosphonyl, silyl, and combinations of the above-mentioned elements.

5. The zinc porphyrin molecule of claim 2 further comprising:
   a first phenyl ring attached to a third meso position from the four zinc porphyrin meso positions, with attached elements $A_1$-$A_5$;
   a second phenyl ring attached to a fourth meso position from the four zinc porphyrin meso positions, with attached elements $B_1$-$B_5$;
   wherein $A_1$, $A_3$, and $A_5$ are hydrogen (H), and $A_2$ and $A_4$ are tert-butyl (($CH_3$)$_3$C); and,
   wherein $B_1$, $B_3$, and $B_5$ are hydrogen (H), and $B_2$ and $B_4$ are tert-butyl (($CH_3$)$_3$C).

6. A zinc porphyrin molecule comprising:
   a zinc porphyrin having four meso positions defined as 5, 10, 15, and 20 meso positions;
   a phenylethnyi group attached to a first meso position from the four zinc porphyrin meso positions;
   a first phenyl ring attached to a second meso position from the four zinc porphyrin macrocycle meso positions, the first phenyl ring including attached elements $A_1$-$A_5$, where $A_1$, $A_3$, and $A_5$ are hydrogen (H), and $A_2$ and $A_4$ are tert-butyl ($CH_3$)$_3$C);
   a second phenyl ring attached to a third meso position from the four zinc porphyrin meso positions, the second phenyl ring including attached elements $B_1$-$B_5$, where $B_1$, $B_3$, and $B_5$ are H and $B_2$ and $B_4$ are tert-butyl (($CH_3$)$_3$C); and,
   a bis(4-dimethylaminophenyl)amino group attached to a fourth meso position from the four zinc porphyrin meso positions.

7. The zinc porphyrin molecule of claim 6 further comprising:
   a carboxyl anchor group attached to a phenyl ring of the phenylethnyl linking element.

8. A zinc porphyrin molecule consisting of:
   a zinc porphyrin having four meso positions defined as 5, 10, 15, and 20 meso positions;
   a phenylethnyi group attached to a first meso position from the four zinc porphyrin meso positions;
   a first phenyl ring attached to a second meso position from the four zinc porphyrin meso positions, the first phenyl ring including attached elements $A_1$-$A_5$, where $A_1$, $A_3$, and $A_5$ are hydrogen (H), and $A_2$ and $A_4$ are tert-butyl ($CH_3$)$_3$C);
   a second phenyl ring attached to a third meso position from the four zinc porphyrin meso positions, the second phenyl ring including attached elements $B_1$-$B_5$, where $B^1$, $B_3$, and $B_5$ are H, and $B_2$ and $B_4$ are tert-butyl (($CH_3$)$_3$C); and,
   a bis(4-dimethylam ophenyl)amino group attached a fourth meso position from the four zinc porphyrin meso positions.

* * * * *

UNITED STATES PATENT AND TRADEMARK OFFICE
CERTIFICATE OF CORRECTION

PATENT NO. : 8,907,081 B2
APPLICATION NO. : 13/117529
DATED : December 9, 2014
INVENTOR(S) : Vail et al.

It is certified that error appears in the above-identified patent and that said Letters Patent is hereby corrected as shown below:

In the Claims,

In Claim 8, column 10, line 52, the term "phenylethnyl" has been incorrectly printed as "phenylethnyi".

Also in claim 8, column 10, line 64, the term "bis(4-dimethylaminophenyl)amino" has been incorrectly printed as "bis(4-dimethylam ophenyl)amino".

Signed and Sealed this
Third Day of March, 2015

Michelle K. Lee
*Deputy Director of the United States Patent and Trademark Office*